United States Patent [19]

Hildebrand et al.

[11] Patent Number: 5,749,845
[45] Date of Patent: May 12, 1998

[54] DELIVERING AN AGENT TO AN ORGAN

[75] Inventors: Keith R. Hildebrand, Houlton, Wis.; J. Edward Shapland, Shoreview, Minn.

[73] Assignee: Iotek, Inc., Minneapolis, Minn.

[21] Appl. No.: 377,845

[22] Filed: Jan. 25, 1995

[51] Int. Cl.$^6$ .................................................. A61N 1/30
[52] U.S. Cl. ................................. 604/21; 604/54; 604/55; 604/102; 606/193
[58] Field of Search ........................... 606/193; 604/96, 604/101–102, 20–21, 2–3, 55

[56] References Cited

U.S. PATENT DOCUMENTS

| | | |
|---|---|---|
| 3,187,248 | 6/1965 | Buckles et al. . |
| 3,918,443 | 11/1975 | Vennard et al. . |
| 4,411,648 | 10/1983 | Davis et al. . |
| 4,430,076 | 2/1984 | Harris ........................................ 604/96 |
| 4,998,930 | 3/1991 | Lundahl . |
| 5,007,897 | 4/1991 | Kalb et al. . |
| 5,222,936 | 6/1993 | Stephen et al. . |
| 5,232,441 | 8/1993 | Stephen et al. . |
| 5,236,413 | 8/1993 | Feiring . |
| 5,301,688 | 4/1994 | Stephen et al. ........................... 604/20 |
| 5,486,160 | 1/1996 | Rossi et al. ............................... 604/21 |

FOREIGN PATENT DOCUMENTS

| | | |
|---|---|---|
| 0 438 078 A2 | 7/1991 | European Pat. Off. . |
| 843 999 | 7/1981 | U.S.S.R. . |
| 1438736 | 11/1988 | U.S.S.R. ................................. 604/96 |
| 2078114 | 1/1982 | United Kingdom .................. 606/193 |
| WO 89/12478 | 12/1989 | WIPO . |
| WO 91/16945 | 11/1991 | WIPO . |
| WO 91/19529 | 12/1991 | WIPO . |
| WO 92/11826 | 7/1992 | WIPO . |

*Primary Examiner*—Mark Bockelman
*Attorney, Agent, or Firm*—Merchant, Gould, Smith, Edell, Welter & Schmidt, P.A.

[57] ABSTRACT

A method of delivering an agent to an organ from the group consisting of a bladder or a uterus. The method utilizes a catheter having an inflatable portion. The inflatable portion of the catheter is inserted into the organ and is inflated so that it expands the organ. The agent is then delivered from the inflatable portion into the wall of the organ. The agent may be prevented from escaping the organ.

23 Claims, 5 Drawing Sheets

DELIVERING AN AGENT TO AN ORGAN

TECHNICAL FIELD

The present invention relates to a catheter for delivering an agent to a hollow organ, and more particularly to a balloon-type catheter that expands a bladder or a uterus.

BACKGROUND

Several medical procedures performed on the bladder, including the treatment of diseases such as bladder cancer and interstitial cystitis, involve instilling a drug solution directly into the bladder. The procedure involves inserting a urinary drainage catheter transurethrally into the bladder. The bladder is drained of urine and then filled with the drug solution. After a specified time, the drug solution is drained from the bladder and the catheter is removed. This procedure is often repeated on a weekly or monthly basis.

Local drug delivery into the bladder by this technique has limited therapeutic efficacy. Drugs merely instilled into the bladder may access the cells lining the bladder, but only a small amount of the drug actually penetrates the bladder lining and reaches the tissue within the bladder wall. This limitation is significant because most bladder diseases involve tissue deep within the bladder wall, not just the superficial portions of the bladder. Cancer is an example of such a disease. Therefore, there is a need for an apparatus and method that penetrates the drug into the bladder wall.

Another limitation with merely filling the bladder with a drug solution is that the drug is not uniformly delivered throughout the bladder. The drug solution will usually contact only the lower portion of the bladder. One technique to deliver the drug to the upper portions of the bladder is to turn the patient upside down. Another technique that is used to deliver drug to the upper portions of the bladder is to overfill the bladder with the drug solution. A problem with this latter technique is that the drug solution becomes pressurized and may flow through the ureters and damage the kidneys.

In addition, the bladder normally has folds of tissue that may prevent the drug from reaching all areas of the bladder wall. The technique of overfilling the bladder with drug solution is also used to deliver drug to areas covered by the folds in the bladder. The pressure from the fluid expands the bladder and removes the folds of tissue. As discussed above, the pressurized drug solution may flow through the ureters and damage the kidneys. Thus, there is a need for an apparatus and method of controlled drug delivery that can deliver the drug to all areas of the bladder.

An additional problem with prior techniques is that the drug only comes into contact with tissue at the surface of the bladder wall. The drug does not penetrate into the bladder wall in order to reach internal tissues that may be diseased or damaged. Thus, there is also a need for an apparatus and method that can deliver the drug to internal tissue beyond the surface of the bladder wall.

Rossi, European Patent Application No. 91100236.8 (Publication No. 0 438 078A2); Stephen et al., U.S. Pat. No. 5,222,936; Stephen et al., U.S. Pat. No. 5,232,441; and Stephen et al., U.S. Pat. No. 5,301,688, all describe the use of an iontophoretic catheter for delivering drugs, dyes, and other agents to the bladder wall. The difficulty with these devices and methods is that they do not prevent the agent from flowing into the ureters and potentially damaging the patient's kidneys. These devices also do not accommodate folds in the bladder wall or other abnormalities. Nor do the devices and methods disclosed in these patents ensure delivery of the drug to the upper portions of the bladder.

Additionally, the way that these devices provide iontophoretic current has several shortcomings. First, there is a danger that the ureters will shunt the electric current away from the bladder wall. Second, there is a danger of high current densities or "hot spots" at defects in the bladder wall. Examples of defects include inflammation, local areas of trauma due to manipulation, and anatomical irregularities such as folds in the bladder tissue. Both shunting and hot spots cause uneven distribution of the drug and decrease the amount of drug delivery to the bladder tissue. Shunting and hot spots can also cause tissue damage. Third, the electrode is difficult to center in the bladder and could be positioned very near the bladder wall. A misaligned electrode also causes a danger of shunting electric current and makes it difficult to provide uniform drug delivery. Thus, there is a need for an iontophoretic catheter that evenly distributes the electric current throughout all areas of the bladder wall.

Additionally, the structure of a uterus and fallopian tubes is similar to the bladder and ureters. Thus, an apparatus and method for delivering drugs to a bladder that overcomes the shortcomings set forth above also would be useful in delivering drugs to the uterus.

SUMMARY

An advantage of the present invention is that it provides an apparatus and method of uniform and controlled delivery of an agent to substantially all areas of the walls in an organ that has a confined chamber. A further advantage is that it causes penetration of the agent into the organ wall.

The present invention provides a method of delivering an agent to an organ from the group consisting of a bladder and a uterus. The method utilizes a catheter having an inflatable portion. The inflatable portion of the catheter is inserted into the organ and is inflated so that it expands the organ. The agent is then delivered from the inflatable portion into the wall of the organ.

These and other advantages and features that characterize the present invention are pointed out with particularity in the claims annexed hereto and forming a further part hereto. However, for a better understanding of the invention, its advantages, and objects obtained by its use, reference should be made (1) to the drawings that form a further part hereto; and (2) to the accompanying descriptive matter, which illustrates and describes embodiments of the present invention.

DETAIL DESCRIPTION

Figure 1A:
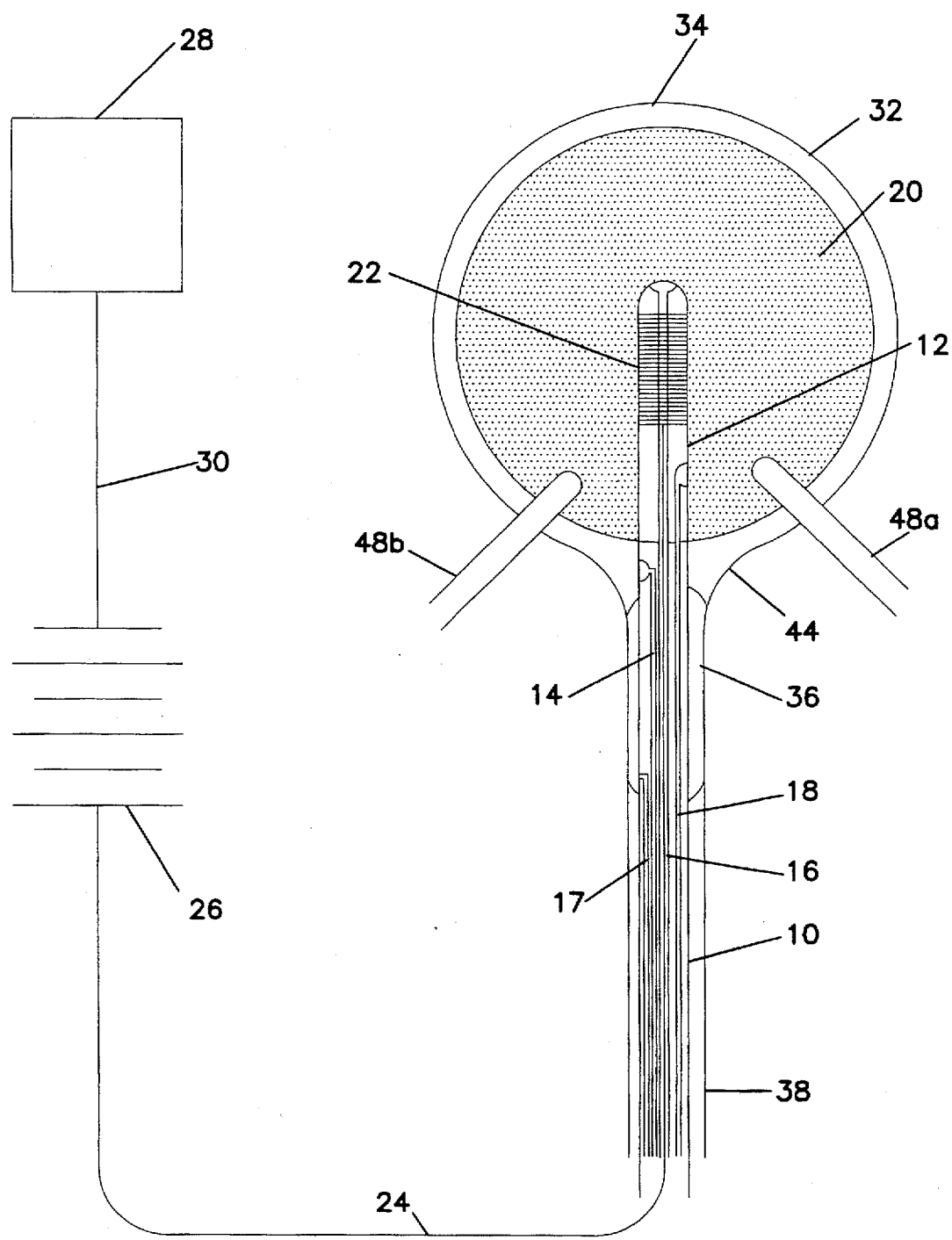
FIG. 1A shows a cross-sectional view of an embodiment that includes a balloon-type catheter for delivering an agent to an organ.

The invention will initially be described in general terms and then the preferred embodiment of the invention will be described in detail with reference to the drawings, wherein like reference numerals represent like parts and assemblies throughout the several views. Reference to the preferred embodiment does not limit the scope of the invention, which is limited only by the scope of the claims.

In general terms, the present invention relates to the delivery of an agent to an organ having a confined chamber such as a bladder or a uterus. A balloon-type catheter is inserted into the organ and inflated, which causes the organ to expand. When expanded, the inner surface of the organ wall conforms to the shape of the inflated balloon. Substantially all of the folds in the organ are removed as it expands. As a result, contact between the inflated balloon and the walls of the organ is substantially uniform and delivery of the agent is enhanced.

For purposes of brevity and clarity, the specification describes the present invention in terms of delivering an agent to a bladder. However, one skilled in the art will realize that the present invention can be used to deliver an agent to other types of organs that have a confined chamber such as a uterus.

For purposes of the specification and claims, the term agent includes all drugs, diagnostic dyes, fixatives, genes, antisense oligonucleotides, therapeutic agents, and other substances that have medical applications. Furthermore, the term agent refers to agents that are in a liquid or solution state.

Referring to FIG. 1A, a balloon-type catheter includes a catheter body 10 that has a distal portion 12, drainage lumen 14, a first inflation lumen 16, a second inflation lumen 17, and a return lumen 18. A delivery balloon 20 having a cavity is attached to the distal portion 12 and is in fluid communication with the first inflation lumen 16 and the return lumen 18.

The delivery balloon 20 is preferably made from a porous membrane having pores sized approximately from 150 angstroms to 500 microns. The most preferred range of pore sizes is approximately from 0.1 micron to 1 micron. The types of material that can be used to form the delivery balloon 20 include polyethylene, polyester, polyurethane, nylon, and silicone. The preferred material is polyester.

Figure 1B:
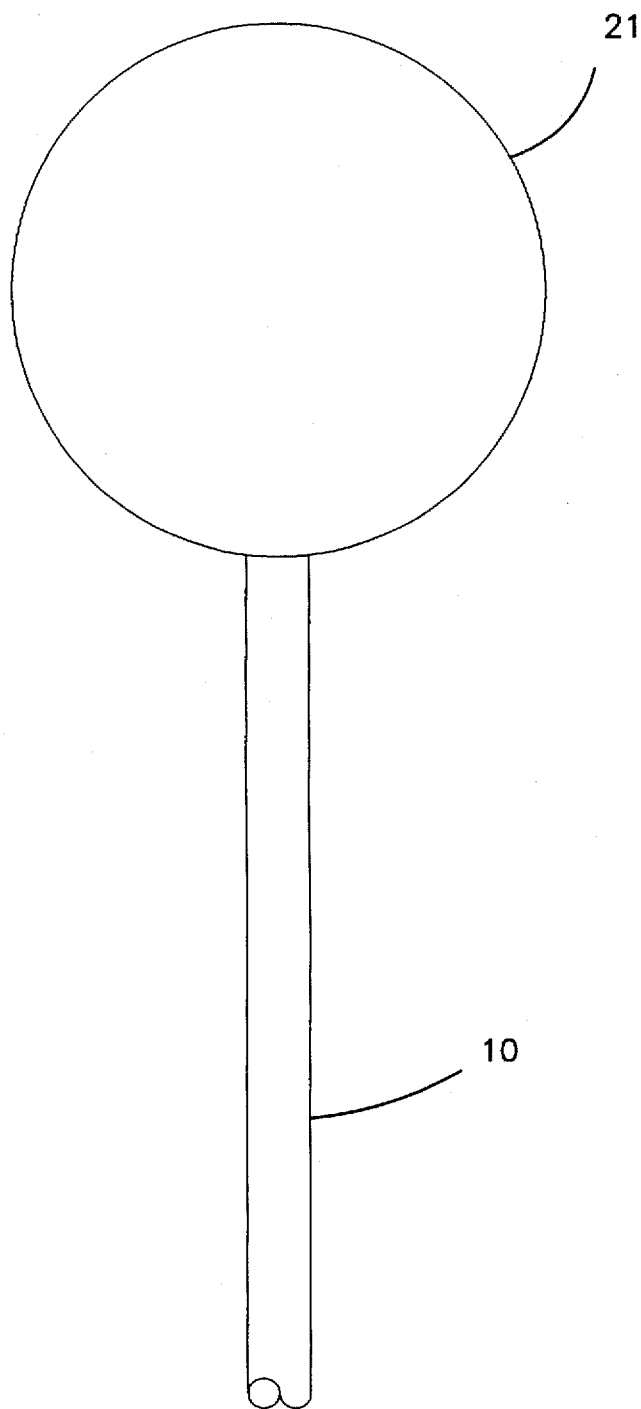
FIG. 1B show a side view of an alternative embodiment of the balloon-type catheter show in FIG. 1.

In one alternative embodiment, as shown in FIG. 1B the surface of the delivery balloon 20 may be coated with a polymer matrix 2. An advantage of the polymer matrix 2 is that it facilitates contact between the delivery balloon 20 and the bladder wall. Additionally, the polymer matrix 2 may contain a drug or an agent such as protamine sulfate or DMSO, which will enhance penetration of the primary therapeutic agent into the bladder wall. Alternatively, the polymer matrix 2 may contain the agent that is to be delivered to the bladder. Polymer matrices are described in more detail in U.S. patent application Ser. No. 07/973,263, filed on Nov. 9, 1992, and entitled POLYMER MATRIX DRUG DELIVERY APPARATUS AND METHOD, which is hereby incorporated by reference.

A first electrode 22 is attached to the distal portion 12 of the catheter body 10 so that it is inside the delivery balloon 20. A first lead 24 is connected to the electrode 22, extends through the first inflation lumen 16, and is then operably connected to a power supply 26. A second electrode 28 is also operably connected to the power supply 26 by a second lead 30. The second electrode 28 is preferably a patch-type electrode that can be affixed to the surface of a patient's skin.

In order to maintain substantially uniform delivery of the agent during iontophoresis, the second electrode 28 should be placed on the patient's body so that it is approximately 6 inches or more from the first electrode 22. Separating the electrodes 22 and 28 by this distance will ensure that the electrical field generated during iontophoresis will pass through substantially all areas of the bladder wall 32. Preferably, the electrode is placed on the patient's thigh.

Alternatively, the balloon-type catheter of the present invention can have a bipolar electrode configuration in which the second electrode is operably connected to the catheter body 10 at a position that is not within the cavity of the delivery balloon 20. Preferably, the second electrode 28 is approximately 4 inches or more from the delivery balloon 20 so that it will not enter the patient's bladder 34 during use and will also generate an electric field that passes through substantially the entire area of the bladder wall during iontophoresis. Bipolar configurations of electrodes are discussed in more detail in U.S. patent application Ser. No. 08/203,811, filed Mar. 1, 1994, and entitled MULTIPLE ELECTRODE DRUG DELIVERY APPARATUS, which is hereby incorporated by reference.

An advantage of a bipolar configuration is that the skin-patch electrode 28 is eliminated. The skin-patch electrode often causes discomfort and/or inflammation because of the skin's high impedance. In contrast, the moist mucosal lining of the urinary tract provides a path for the electric current that has much less impedance. When there is a lower impedance, one skilled in the art will realize that a lower voltage should be used in order to control the current and prevent damage to the tissue. Additionally, there is greater control of the electric field generated by a bipolar configuration.

A blocking portion includes a blocking balloon 36 that operatively connected to the catheter body 10 and is in fluid communication with the second inflation lumen 17. The blocking balloon 36 serves to prevent substantially all of the agent delivered from the delivery balloon 20 to the bladder 34 from escaping into the urethra 38. The blocking balloon 36 is preferably made from an impermeable material.

Figure 2:
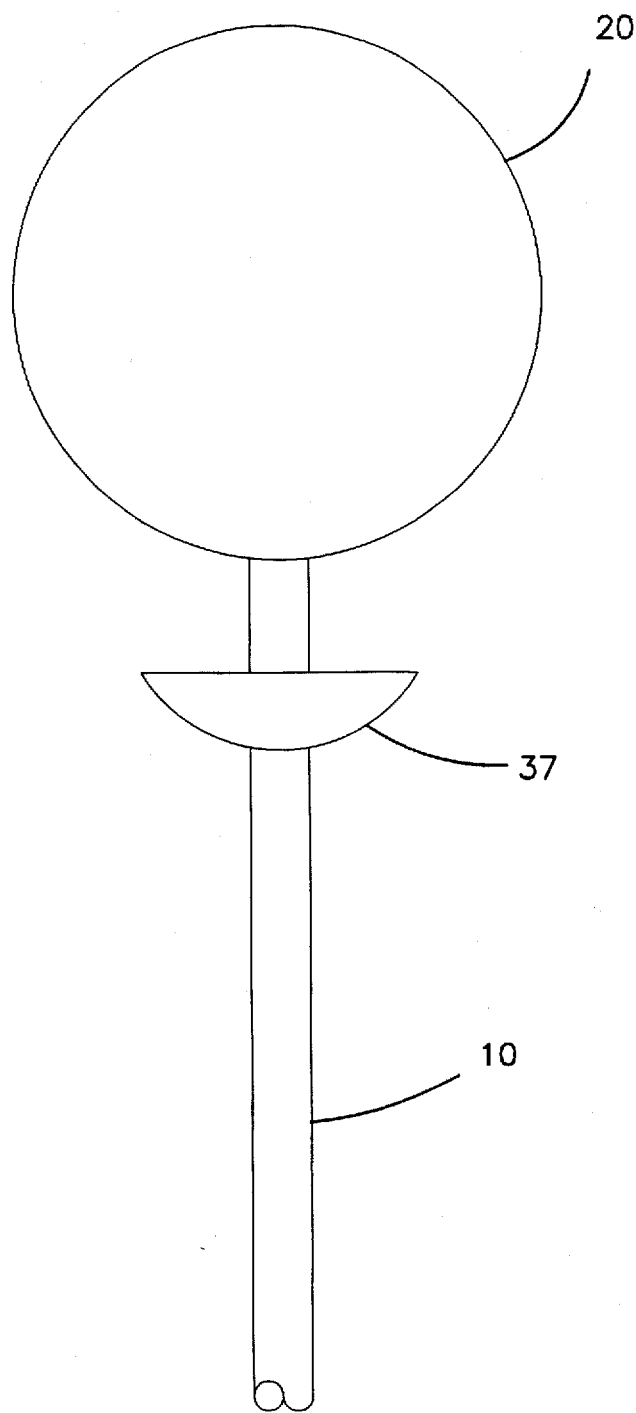
FIG. 2 shows a side view of an alternative embodiment of the balloon-type catheter shown in FIG. 1.

Referring to FIG. 2, the embodiment shown in FIG. 1 is adaptable for use in a uterus. In such an alternative embodiment, the blocking portion may include a cap 37 that is mounted on the catheter body 10 rather than the blocking balloon 36. The cap 37 fits over the cervix and functions as a barrier that blocks the opening of the cervix and prevents substantially all of the agent from passing into the vagina. The cap 37 is similar to a diaphragm that is often used for birth control and can be sized to fit a particular size of cervix.

Figure 3:
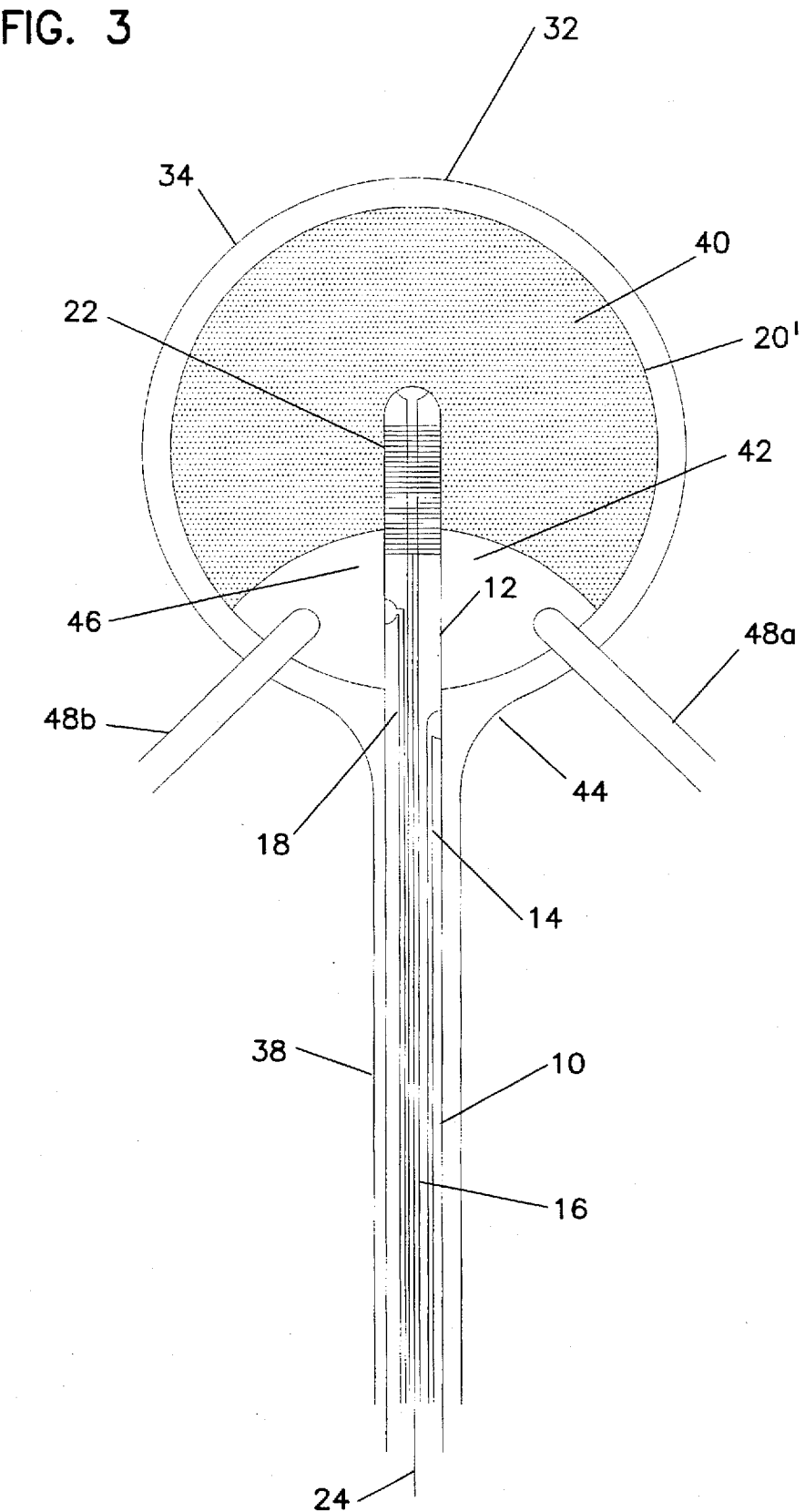
FIG. 3 shows a cross-sectional view of another alternative embodiment of the balloon-type catheter shown in FIG. 1.

Referring to FIG. 3, an alternative embodiment has a delivery balloon 20' that has a porous portion 40 and an impermeable portion 42. The impermeable portion 42 is oriented so that it is adjacent to the neck 44 of the bladder 34 during use. When the balloon 20' is inflated, the impermeable portion 42 presses against the portion of the bladder wall 32 surrounding the opening of the urethra 38 and prevents the agent that is in the bladder 34 from passing into the urethra 38. The impermeable portion 42 replaces the blocking balloon 36 and second inflation lumen 17 of the embodiment shown in FIG. 1 and described above.

Preferably, the impermeable portion 42 is sized so that it is also adjacent to the trigone area 46 of the bladder 34. In this embodiment, the impermeable portion 42 would also press against the trigone area 46 and hence the openings to the ureters 48a and 48b. As a result, substantially all of the urine produced by the kidneys would be prevented from entering the bladder 34, and the drug will not be contaminated with urine or electrolytes, which could decrease efficiency of the iontophoresis. Additionally, minimal drug will be lost into the ureters, which will minimize waste.

One skilled in the art will realize that the embodiment shown in FIG. 3 is also adaptable for use in a uterus. In this alternative embodiment, the impermeable portion 42 is sized and positioned to block the opening of the patient's cervix and the opening of the patient's fallopian tubes. Thus, substantially all of the agent is prevented from flowing through the cervix and into the fallopian tubes. In this alternative embodiment, there is not a need for either the blocking balloon 36 or the diaphragm-like cap that was described above.

Figure 4:
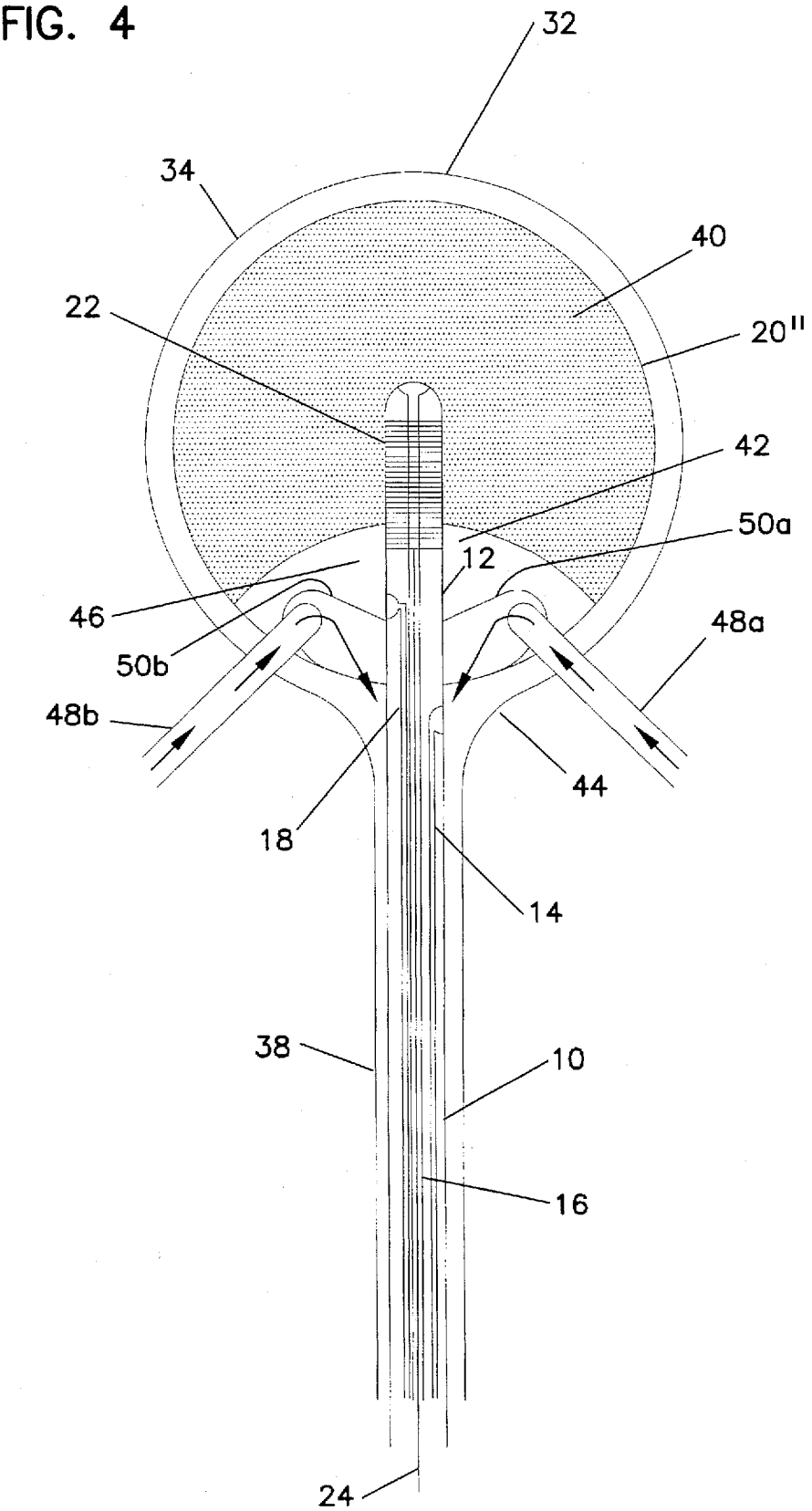
FIG. 4 shows a cross-sectional view of yet another alternative embodiment of the balloon-type catheter shown in FIG. 1.

In another alternative design, as shown in FIG. 4, the delivery balloon 20" can define channels 50a and 50b, which funnel urine from the ureters 48a and 48b to the drainage lumen 14. During treatment, any urine that is produced by the kidneys would pass from the ureters 48a and 48b, through the channels 50a and 50b, and into the drainage lumen 14. Thus, urine would be prevented from collecting in the bladder 34 during the medical procedure. Alternatively, the channels 50a and 50b could funnel the urine to a second drainage lumen, not shown.

There are several ways to form the channels 50a and 50b. One way to form the channels 50a and 50b is to use one material for the area of the delivery balloon 20" that forms the channels and another material for the other areas of the delivery balloon 20". The material that forms the channels 50a and 50b would be less elastic relative to the material used to form the other areas of the delivery balloon 20".

Another way to form the channels 50a and 50b is to form the balloon with materials having a different thickness. The material used to form the channels 50a and 50b would be thicker than the material used to form the other areas of the delivery balloon 20". Alternatively, channels 50a and 50b could be formed by contours in the delivery balloon 20". The contours can be molded into the delivery balloon 20".

In use, the catheter body 10 is inserted through the urethra 38 until the distal portion 12 and hence the delivery balloon 20 is located in the patient's bladder 34. Urine within the bladder 34 is drained through the drainage lumen 14. If the embodiment of FIG. 1 is used, the blocking balloon 36 is inflated so that it will prevent substantially all of the agent from entering the urethra 38. The delivery balloon 20 is then inflated with the desired agent. The bladder wall expands with the delivery balloon 20 and conforms to the shape of the inflated delivery balloon 20.

Upon inflation of the delivery balloon 20, a minute amount of agent will permeate through the porous membrane that forms the delivery balloon 20 and form a micro-thin layer of agent between the delivery balloon 20 and the bladder wall 32. The size and distribution of the pores in the delivery balloon 20 should allow just enough solution to pass through to create the micro-thin layer and still allow sufficient pressure to be maintained in the delivery balloon 20 to keep it inflated. If the embodiments of either FIG. 3 or FIG. 4 are used, the layer should be thin enough to maintain the seal between the impermeable portion and the bladder wall and thus minimize fluid escape from the bladder.

The micro-thin layer will help maintain contact between the delivery balloon 20 and substantially all areas of the bladder wall 32. Additionally, forming the micro-thin layer of solution in combination with expanding the bladder 34 will permit the electric field during iontophoresis to be evenly distributed throughout the bladder wall 32. The micro-thin layer of solution will provide a conductive path between substantially all areas of the delivery balloon 20 and substantially all areas of the bladder wall 32. Thus, the electric field will be evenly distributed throughout the bladder wall 32 and hot spots will be prevented.

If the balloon-type catheter is used to treat bladder cancer, the preferred agents are BCG (Bacillus Calmette Guerin), thiotepa, doxorubicin, mitomycin C, interferon, bleomline, cisplatimun, vinca alkaloids, or porphyrin. If interstitial cystitis is treated, the preferred agents are pentosanpolysulfate, heparin, substance P, or dimethyl sulfoxide. If the balloon-type catheter is used to deliver an anesthetic agent prior to conducting surgery or a biopsy, the preferred agents are lidocaine or bupivacaine. Penetration enhancers can be used to assist delivery of the agent to internal tissue. Examples of penetration enhancers include DMSO, protamine sulfate, and cyclodextrin. Although specific treatments and agents are listed, one skilled in the art will realize that the apparatus and method of the present invention can be used for a variety of medical procedures and agents.

Iontophoresis is conducted after the delivery balloon 20 is expanded and the micro-thin layer of agent is formed. Specifically, the circuit between the power supply 26, the first electrode 22, and the second electrode 28 will be closed so that an electric current will flow through the delivery balloon 20 and bladder wall 32. The current will deliver the agent from the interior of the delivery balloon 20, through the membrane that forms the delivery balloon 20, and into the bladder wall 32. The current is stopped after a specified time interval. The time interval is preferably long enough to allow the proper dosage of agent to be delivered into the wall 32 of the patient's bladder. Iontophoresis is discussed in more detail in U.S. patent application Ser. No. 08/166,737, filed Dec. 14, 1993, and entitled INTERNAL IONTOPHORESIS DRUG DELIVERY APPARATUS AND METHOD, which is hereby incorporated by reference.

One skilled in the art will realize that other means, including other types of phoresis, can be used to deliver the agent from the delivery balloon 20 into the bladder wall 32. Other types of phoresis include phonophoresis. In a phonophoresis embodiment, an ultrasonic transducer would replace first electrode 22. Second electrode 28 is not required in this embodiment.

One skilled in the art will further realize that electroporation can also be used to increase the permeability of the tight epithelium that lines the urinary tract so that the agent may more easily penetrate this barrier and thus enhance delivery of the agent. A bipolar configuration is preferably used for performing electroporation. Electroporation is discussed in more detail in U.S. patent application Ser. No. 08/129,252, filed Sep. 29, 1993, entitled ELECTROPORATION ENHANCED IN VIVO DRUG DELIVERY, which is hereby incorporated by reference.

One skilled in the art will further realize that heating could be used to enhance the cellular uptake of the drug and hence the therapeutic effect of the drug. In this embodiment, a heating element would be operably connected to the distal portion 12 of the catheter body 10.

Delivery of the agent is preferably accomplished in a single inflation and delivery. As previously discussed, however, iontophoretic delivery could be compromised if urine collects in the bladder 34. Thus, delivery of the agent may be accomplished with multiple inflations and deliveries. Accumulated urine would be drained in between inflations of the delivery balloon 20. Urine input into the bladder 34 averages about 1 ml/min. Thus, this technique will be most useful if the embodiment of the delivery balloon 20 (e.g., FIG. 1) does not block the openings to the ureters 48a and 48b or have channels 50a and 50b to route urine from the ureters 48a and 48b to the drainage lumen 14.

As discussed above, the delivery balloon 20, 20', or 20" may be coated with a polymer matrix. The polymer matrix may be used to facilitate contact between the delivery balloon 20, 20', or 20". In this embodiment, the polymer matrix provides substantially uniform contact between the surface of the balloon and the bladder wall. Additionally, the polymer matrix can contain a penetration enhancer and/or the agent itself.

In the embodiments shown in FIG. 3 and 4, the polymer matrix can be arranged and configured in several different ways in order to prevent the agent or penetration enhancer from escaping into the urethra or the ureters. In one possible configuration, the polymer matrix coats only the area of the balloon 20' or 20" that has pores and does not coat the impermeable portion 42. In another possible configuration, the polymer matrix coats the entire balloon 20' or 20", but the portions of the polymer matrix that covers the impermeable portion 42 does not embody the agent or the penetration enhancer.

While the invention has been described in conjunction with a specific embodiment thereof, it is evident that different alternatives, modifications, steps, techniques, and variations will be apparent to those skilled in the art in view of the foregoing description. Accordingly, the invention is not limited to these steps, embodiments, or the use of elements having specific configurations and shapes as presented herein.

The invention that we claim is:

1. A method of delivering an agent from a catheter having an inflatable portion to an organ from the group consisting of a bladder and a uterus, the organ having an inner surface and folds of tissue along the inner surface, the method comprising the steps of:
   (a) inserting the inflatable portion of the catheter into the organ;
   (b) inflating the inflatable portion so that it expands the organ and removes folds of tissue along the inner surface of the organ; and
   (c) delivering the agent from the inflatable portion into the wall of the organ.

2. The method of claim 1 wherein the step of inflating the inflatable portion includes substantially conforming the inner surface of the organ wall to the shape of the inflatable portion.

3. The method of claim 1 wherein the catheter further includes a first electrode being inside the inflatable portion of the catheter and a second electrode being in contact with the patient's body, further wherein the step of delivering the agent includes supplying an electric current between the first and second electrodes.

4. The method of claim 3 comprising the additional step of placing the second electrode against the skin of the patient's body before the electric current is supplied between the first and second electrodes.

5. The method of claim 1 wherein the step of inflating the inflatable portion of the catheter includes injecting the agent into the inflatable portion.

6. The method of claim 5 wherein the inflatable portion of the catheter has an interior, further wherein the step of delivering the agent includes causing the agent to pass from the interior of the inflatable portion and into the organ wall.

7. The method of claim 1 wherein the inflatable portion of the catheter has a polymer matrix and the polymer matrix embodies a second agent, the method comprising the additional step of delivering the second agent from the polymer matrix and into the organ wall.

8. The method of claim 1 wherein the inflatable portion of the catheter has a polymer matrix and the polymer matrix embodies the agent, further wherein the step of delivering the agent includes causing the agent to be released from the polymer matrix and pass into the organ wall.

9. The method of claim 1 comprising the additional step of providing a layer of the agent between the inflatable portion of the catheter and the organ wall.

10. The method of claim 1 wherein the organ is a bladder and the method comprises the additional step of preventing substantially all of the agent from flowing into the patient's urethra.

11. The method of claim 10 wherein the catheter includes a blocking portion that is inflatable, further wherein the step of preventing substantially all of the agent from flowing into the patient's urethra includes the steps of:
   (a) inserting the blocking portion of the catheter into the urethra so that it is proximate the bladder; and
   (b) inflating the blocking portion so that it substantially blocks substantially all of the urethra.

12. The method of claim 1 wherein the organ is bladder and the method comprises the additional step of preventing substantially any urine from accumulating in the bladder.

13. The method of claim 12 wherein the step of preventing substantially any urine from accumulating in the bladder comprises blocking the urters so that substantially no urine can flow the bladder from the ureters.

14. The method of claim 1 wherein the organ is a bladder and the method comprises the additional step of draining urine from the bladder before the step of delivering the agent.

15. The method of claim 14 comprising the additional steps of:
   (a) deflating the inflatable portion of the catheter after the step of delivering the agent; and
   (b) repeating the steps of draining urine, inflating the inflatable portion, and delivering the agent.

16. The method of claim 1 wherein the organ is a uterus and the method comprises the additional step of preventing substantially all of the agent from flowing into the patient's vagina.

17. The method of claim 16 wherein the catheter includes a blocking portion, further wherein the step of preventing substantially all of the agent from flowing into the patient's vagina includes the step positioning the blocking portion so that it substantially blocks the opening of the cervix.

18. The method of claim 17 wherein the blocking portion is a cap that fits over the cervix and the step of positioning the blocking portion includes the step of positioning the cap over the cervix.

19. The method of claim 1 wherein the organ is a uterus and the method comprises the additional step of preventing substantially all of the agent from flowing into the patient's fallopian tubes.

20. A method of delivering an agent from a catheter having an inflatable portion to a patient's bladder, the catheter including a first electrode inside the inflatable portion and a second electrode in contact with the patient's body, the method comprising the steps of:
   (a) inserting the inflatable portion of the catheter into the bladder;
   (b) inflating the inflatable portion so that it expands the bladder, thereby substantially conforming the inner surface of the bladder wall to the shape of the inflated inflatable portion;
   (c) preventing substantially all of the agent from flowing into the patient's urethra;

(d) preventing substantially any urine from accumulating in the bladder; and (e) supplying an electric current between the first and second electrodes thereby delivering the agent from the inflatable portion and into the wall of the bladder.

21. A method of delivering an agent from a catheter having an inflatable portion to a patient's bladder, the catheter including a first electrode inside the inflatable portion and a second electrode in contact with the patient's body, the method comprising the steps of:

(a) inserting the inflatable portion of the catheter into the bladder;

(b) injecting the agent into the inflatable portion so that the inflatable portion inflates and expands the bladder, thereby substantially conforming the inner surface of the bladder wall to the shape of the inflated inflatable portion;

(c) preventing substantially all of the agent from flowing into the patient's urethra;

(d) preventing substantially any urine from accumulating in the bladder; and (e) supplying an electric current between the first and second electrodes thereby delivering the agent from the inflatable portion and into the wall of the bladder.

22. A method of delivering an agent from a catheter having an inflatable portion to a patient's uterus, the catheter including a first electrode inside the inflatable portion and a second electrode in contact with the patient's body, the method comprising the steps of:

(a) inserting the inflatable portion of the catheter into the uterus;

(b) injecting the agent into the inflatable portion so that the inflatable portion inflates and expands the uterus, thereby substantially conforming the inner surface of the uterus wall to the shape of the inflated inflatable portion;

(c) preventing substantially all of the agent from flowing through the patient's cervix;

(d) preventing substantially all of the agent from flowing into the patient's fallopian tubes; and (e) supplying an electric current between the first and second electrodes thereby delivering the agent from the inflatable portion and into the wall of the uterus.

23. A method of delivering an agent from a catheter to a bladder, the catheter having an inflatable portion and a drainage lumen, the inflatable portion defining channels that extend from the ureters to the drainage lumen, the method comprising the steps of:

(a) inserting the inflatable portion of the catheter into the organ;

(b) inflating the inflatable portion so that it expands the organ;

(c) delivering the agent from the inflatable portion into the wall of the organ; and (d) channeling substantially all of the urine from the ureters to the drainage lumen.

* * * * *